United States Patent [19]

Franks

[11] 4,215,212

[45] Jul. 29, 1980

[54] REGENERATED CELLULOSE CONTAINING CROSS LINKED SODIUM LIGNATE OR SODIUM LIGNOSULFONATE

[75] Inventor: Neal E. Franks, Suffern, N.Y.

[73] Assignee: Akzona Incorporated, Asheville, N.C.

[21] Appl. No.: 27,977

[22] Filed: Apr. 9, 1979

Related U.S. Application Data

[60] Division of Ser. No. 887,793, Mar. 17, 1978, which is a continuation-in-part of Ser. No. 706,995, Jul. 20, 1976, abandoned.

[51] Int. Cl.$^2$ .................... C08B 15/10; C08B 16/00; D01F 2/00
[52] U.S. Cl. ................. 536/57; 106/123 R; 106/123 LC; 260/17.4 CL; 260/17.5; 536/60; 536/61
[58] Field of Search ............ 536/57, 60, 61; 260/17.4 CL, 17.5; 106/123 R, 123 LC; 264/188, 187, 191

[56] References Cited

U.S. PATENT DOCUMENTS

| | | | |
|---|---|---|---|
| 2,265,563 | 12/1941 | Kirkpatrick | 264/331 |
| 2,796,656 | 6/1957 | Schappel et al. | 264/191 |
| 3,109,698 | 11/1963 | Klein et al. | 264/191 |
| 3,242,120 | 3/1966 | Steuber | 106/123 R |
| 3,395,033 | 7/1968 | Remer | 260/17.5 |
| 3,423,167 | 1/1969 | Kuzmak | 264/191 |
| 3,463,699 | 8/1969 | Broadhead et al. | 106/123 R |
| 3,600,308 | 8/1971 | Allan | 210/52 |
| 3,844,287 | 10/1974 | Smith | 260/17.4 CL |
| 3,919,385 | 11/1975 | Smith | 260/17.4 CL |
| 3,940,352 | 2/1976 | Wennerblom et al. | 260/17.5 |
| 4,064,081 | 12/1977 | McCoy et al. | 260/17.5 |

FOREIGN PATENT DOCUMENTS 42-23982 4/1967 Japan ...................... 264/182

*Primary Examiner*—Ronald W. Griffin
*Attorney, Agent, or Firm*—Francis W. Young; Jack H. Hall

[57] ABSTRACT

Regenerated cellulose products containing formaldehyde cross linked sodium lignate or sodium lignosulfonate in an amount of from about 1% to about 40% by weight based on the weight of the cellulose in the product are prepared by mixing one of the cross linked lignin derivatives or a mixture thereof substantially uniformly in a viscose solution and extending the solution into a spin bath in which the extruded viscose streams coagulate into filaments containing the cross linked lignin derivative. The extended regenerated product may be used as a fiber in absorbent cellulose products such as diapers, sanitary napkins, tampons and the like.

6 Claims, No Drawings

REGENERATED CELLULOSE CONTAINING CROSS LINKED SODIUM LIGNATE OR SODIUM LIGNOSULFONATE

This is a division of application Ser. No. 887,793, filed Mar. 17, 1978, which is a continuation-in-part of Ser. No. 706,995, filed July 20, 1976, now abandoned.

This invention relates generally to regenerated cellulose and more particularly to polymer extended regenerated cellulose products such as rayon filaments and fibers prepared by the viscose process.

In accordance with the viscose process, chemical cellulose is converted into rayon by a series of steps in which the cellulose is first treated with sodium hydroxide solution to mercerize it and form alkali cellulose. The alkali cellulose, after aging, is reacted with carbon disulfide to form the soluble sodium xanthate derivative. The xanthated cellulose is later dissolved in dilute aqueous sodium hydroxide to form viscose which, after ripening, is spun by extrusion through a spinnerette into a spin bath containing sulfuric acid and salts which coagulate the streams of viscose solution into individual filaments of regenerated cellulose. These filaments may be formed into a thread, bunched into a tow or they may be collected as a cake of a mass of filaments depending upon the particular type of product desired.

It has been proposed heretofore to prepare regenerated cellulose fibers which contain synthetic polymers. These polymers may be included in the fibers to improve their absorbency or to alter other properties of the fibers. Alloy fibers containing regenerated cellulose and polyacrylic acid salts are disclosed, for example, in U.S. Pat. No. 3,844,287 and regenerated cellulose fibers containing regenerated cyanoethyl cellulose and polyvinyl pyrrolidone are disclosed in U.S. Pat. No. 3,919,385. It has also been proposed in U.S. Pat. No. 2,265,563 to include a lignin resin in a molded cellulose product but lignin cannot be successfully included in products of the viscose process because it leaches from the filament during coagulation.

It is therefore an object of this invention to provide a novel regenerated cellulose fiber containing a lignin derivative as polymeric extender. Another object of the invention is to provide a regenerated cellulose fiber prepared by the viscose process which contains a relatively inexpensive lignin polymer as an extender and is adapted to be used in textiles or as a staple fiber. A more specific object of the invention is to provide a regenerated cellulose fiber having physical characteristics which are acceptable particularly for use in making textiles and mats of staple fibers at a raw material cost which is less than that of the conventional substantially pure rayon fiber. A still further object of the invention is to provide a process for making extended regenerated cellulose products by the viscose process which are adapted for use in textiles and for making staple fiber products.

The foregoing objects and others are accomplished in accordance with this invention, generally speaking, by providing regenerated cellulose products containing a significant amount of sodium lignate or sodium lignosulfonate which has been cross linked by chemical reaction with formaldehyde until it is substantially insoluble in the coagulating bath used to regenerate cellulose in a xanthate process. Ether derivatives of the cross linked product may also be incorporated in the regenerated cellulose in accordance with the invention. It has been found that substantially water insoluble formaldehyde cross linked sodium lignate and formaldehyde cross linked sodium lignosulfonate and their esters can be dispersed substantially uniformly in a viscose solution prior to extrusion and that the cross linked product will be retained in the filament after coagulation in conventional coagulating baths. The retention of formaldehyde cross linked sodium lignate by the filament after processing is almost quantitative in amounts of up to 40% by weight based on the weight of cellulose in the viscose solution. The retention of formaldehyde cross linked sodium lignosulfonate by the filament after processing is good in amounts of up to 20% by weight and more but at 40% by weight it is much poorer than the retention of formaldehyde cross linked sodium lignate. Hence, when a filament or other shaped article of regenerated cellulose containing as much as 40% by weight formaldehyde cross linked lignin derivative is desired it is recommended that either formaldehyde cross linked sodium lignate, or an aliphatic ether thereof be used or that a mixture thereof with formaldehyde cross linked sodium lignosulfonate be used. Any amount of the formaldehyde cross linked product will have some effect on the filament but, in most instances, quantities of less than 1% will not significantly affect the cost of the filament so for practical purposes the invention contemplates a pellicular shaped product prepared by the viscose process and containing from about 1% to about 40% of formaldehyde cross linked sodium lignate, sodium lignosulfonate, aliphatic ethers thereof, or mixtures thereof based on the weight of cellulose in the viscose solution.

The novel regenerated cellulose fiber may be prepared by a process wherein the cross linked reaction product of formaldehyde and sodium lignate or lignosulfonate or an ether thereof is injected or otherwise mixed with an extrudable viscose solution prior to extrusion through a spinnerette in an amount of from about 1% to about 40% by weight based on the weight of the cellulose in the viscose solution, the resulting mixture is extruded through a spinnerette into a conventional coagulating bath containing sulfuric acid and conventionally used salts. The resulting filaments may be stretched, collected by a suitable means, purified and finished by a series of steps conventionally used in making filaments by the viscose process. The cross linked sodium lignate or sodium lignosulfonate is preferably injected into the viscose solution just prior to spinning or it may be incorporated in the cellulose xanthate solution by mixing it with the alkali cellulose used to prepare the viscose solution.

The regenerated cellulose product containing formaldehyde cross linked sodium lignate or formaldehyde cross linked sodium lignosulfonate has a yellow color imparted thereto by the cross linked polymer additive which may be removed, if desired, by any suitable bleaching process, such as, for example, with an alkaline peroxide bleach. In those applications where color of the product is unimportant, the bleaching step can be omitted. The cross linked sodium lignate and sodium lignosulfonate contain phenolic groups which may be etherified by any suitable process such as by reaction with acrylonitrile, ethylene oxide, propylene oxide or the like to form an aliphatic ether or the cross linked polymer may be reacted with a reducing agent such as sodium borohydride or the like. The resulting product will be more receptive to reactions designed to remove the yellow color.

The spun regenerated fiber may be processed by conventional washing, stretching, carding, drying and the like processes.

The regenerated cellulose fiber provided by the invention can be used in the form of a continuous filament in making various types of fabrics while the staple fiber can be used in various types of cellulose products such as, for example, diapers, wiping cloths, sanitary napkins, tampons and the like. The fiber may also be carbonized to produce a carbon fiber. Lignin contains 65 to 68% by weight carbon and cellulose contains about 44% carbon so the addition of one of the lignin derivatives to the fiber not only extends it but also increases its carbon content.

The sodium lignate and sodium lignosulfonate may be cross linked by reaction with formaldehyde in accordance with any suitable process which will produce a product which is substantially insoluable and non-reactive with the constitutents of the coagulating bath used in the viscose process. A suitable process is disclosed in U.S. Pat. No. 3,600,308.

To obtain a sodium lignate insoluble in the coagulating bath and in water so that the material is not leached out during the washing steps, a least about 3.8% by weight of formaldehyde must be cross-linked with the lignate. The maximum amount of formaldehyde that can be cross-linked with sodium lignate is limited by the maximum pourable viscosity of the product. With more than about 10% formaldehyde, sodium lignate becomes to viscous. With sodium lignosulfonate at least about 10% formaldehnyde must be used up to a maximum of about 20%.

As stated hereinbefore the cross linked sodium lignate or sodium lignosulfonate must be substantially insoluble in the coagulating bath. The degree of cross linking required to convert the sodium lignate or sodium ligrosulfonate to an insoluble polymer will vary somewhat from one type sodium lignate or sodium lignosulfonate to the other. The results obtained so far indicate that the sulfur content of the sodium lignate or sodium lignosulfonate should be not more than 5% by weight to provide consistently a formaldehyde cross linked polymer which is substantially insoluble in coagulating baths conventionally used in the viscose process. The invention is applicable to all conventional viscose spining processes in which the cross linked polymer is substantially insoluble. For example, the viscose solution may contain prior to the addition of the cross linked lignin polymer from about 5% to about 10% by weight cellulose, about 4% to about 8% sodium hydroxide and 1.7% to about 2.5% sulfur or any other suitable concentrations. The coagulating bath may contain from about 5% to about 15% by weight sulfuric acid, about 5% to about 20% sodium sulfate, about 0% to about 5% by weight magnesium sulfate and about 0% to about 5% by weight zinc sulfate dissolved in water.

Analytical data obtained on a commercially available sodium lignate and two sodium lignosulfonates are shown in Table I. All percentages in the Table are percentages by weight of lignin derivative. The sodium lignosulfonate containing 7.3% total sulfur could not be cross linked with formaldehyde to the point where it was insoluble in the coagulating bath so the one having 2.6% sulfur was used in Examples 7 and 8.

TABLE I

| Properties of Lignin Derivatives | | | |
|---|---|---|---|
| | Sodium Lignate* | Sodium Lignosulfonate I** | Sodium Lignosulfonate II*** |
| Moisture Content (% $H_2O$) | −4 | 8 | 7 |
| Total Sulfur, % | 1.6 (as ether) | 2.6 | 7.3 |
| Sulfate Sulfur as S, % | 0 | 0.1 | 1.0 |
| Sulfite Sulfur as S, % | 0 | 0 | 0.12 |
| CaO, % | Nil | 0.03 | 0.55 |
| MgO, % | Nil | Trace | 0.3 |
| Reducing Sugars, % | Nil | 0 | 0.8 |
| $OCH_3$, % | | 12.7 | 7.7 |
| pH in water of Slurry or Solutions | 6 | 8.5–9.2 | 7.5–8.5 |

*Commercial Product Indulin AT of Westvaco Chemical Division, North Charleston, S.C.
**Commercial Product Marasperse CB of American Can Company, Greenwich, Connecticut
***Commercial Product Marasperse N-22 American Can Company, Greenwich, Connecticut In the following examples which illustrate typical embodiments of the invention, all parts are by weight unless otherwise specified;

EXAMPLE 1

In order to demonstrate that a formaldehyde cross linked sodium lignosulfonate will coagulate in a viscose spin bath, sodium lignosulfonate was cross linked with formaldehyde by suspending about 45 parts of sodium lignosulfonate in about 90 parts of distilled water and mixing the suspension with an aqueous solution of sodium hydroxide in an amount required to adjust the pH to about 11. About 4.5 parts paraformaldehyde were added to the suspension and the resulting mixture was heated and refluxed with stirring for a period of about eight hours. A portion of the resulting product was poured into a typical rayon spin bath containing about 5.5% by weight sulfuric acid, about 24% by weight sodium sulphate and about 1% zinc sulphate. A precipitate formed and the suspension was stirred for about two hours. The coagulated material was separated from the liquid phase by suction filtering and was washed with distilled water. The resulting gummy product was dried at 120° C. and the percentage by weight carbon, hydrogen and sulfur was determined to be about 60.92%, carbon, 4.81% hydrogen and 2.73% sulfur.

EXAMPLE 2

About 900 parts sodium lignosulfonate were dispersed with stirring in about 1800 parts of distilled water. A 50% by weight aqueous sodium hydroxide solution was added until the pH of the suspension was about 11 (about 50 to 60 parts NaOH solution were required). The resulting solution was transferred to a vessel equipped with a reflux condenser and stirrer. About 90 parts paraformaldehyde were added with stirring and the mixture was allowed to set overnight at room temperature. The next morning the mixture was refluxed with stirring for about six hours. At that point, the external heating was stopped and the mixture was permitted to stand at room temperature for another 72 hours. The solution was then ready for mixing with the viscose solution and was placed in a suitable container for storage.

EXAMPLE 3

An aqueous solution containing about 96 parts of sodium hydroxide in about 3080 parts of distilled water was heated under reflux to a temperature of about 60° C. About 824 parts of sodium lignate were added in four equal portions to the solution while it was being stirred vigorously. About 2 parts of a commercially available foam preventing agent, Ocenol, were added, Nitrogen was bubbled through the heated mixture for several hours until the evolution of ammonium and sulfur by-products had practically ceased. About 32 parts of paraformaldehyde were added and the mixture was refluxed for about 3 ½ hours. About 160 parts of 21% aqueous sodium hydroxide solution were added to reduce the viscosity of the solution containing the reaction product of paraformaldehyde and sodium lignate. About 100 parts of the solution were added to about 1400 parts of a spin bath having the composition of that of Example 1 and the precipitate was recovered by filtration after 30 minutes stirring. The cross linked material was washed with about 2000 parts of distilled water and was dried at a temperature of about 120° C. until the weight remained substantially constant. The solids content was about 17.75% by weight. The carbon content of the product was about 66.6% and the hydrogen content was about 5.8%. The product was insoluble in a 5% aqueous sodium hydroxide solution which is ordinarily used in making sulfur determinations.

EXAMPLE 4

A solution of non-cross linked sodium lignate was prepared as in Example 3 except the paraformaldehyde was omitted. The solids content was about 20.22%. The solution has a pH of 13.3. Analytical values of the product from the spin bath were 66.82% carbon, 5.88% hydrogen and 1.09% sulfur without a detectable amount of sodium.

EXAMPLE 5

A suspension of sodium lignate was prepared by adding 824 parts of sodium lignate, with stirring, to 3000 parts distilled water containing sufficient foam preventing agent, about 5 parts Ocenol, and 5 parts of surfactant, Tween 20. The resulting suspension was heated at reflux temperature for one hour while nitrogen was bubbled therethrough. The temperature was then reduced to about 55° to 60° C. and about 16 parts of sodium hydrosulfite were added to the stirred mixture. After about 1 hour at about 55° to 60° C, the mixture was heated under reflux conditions for an additional hour. The mixture was cooled and about 96 parts of flake sodium hydroxide were added slowly to the stirred mixture. Ammonia was evolved and the sodium lignate dissolved during the sodium hydroxide addition.

The mixture was refluxed while the nitrogen purging was continued to remove the greatest portion of the ammonia. After 2 hours of refluxing, about 32 parts of paraformaldehyde were added and the mixture was refluxed for an additional 2 hours. The external heat was then removed and the vessel was cooled for about 16 hours. Acrylonitrile was added with stirring to the cross linked sodium lignate. The mixture was heated at reflux for 90 minutes before adding about 32 parts of sodium hydroxide dissolved in distilled water. The mixture was cooled and held for spinning.

A 100 part portion of the solution was poured into about 1400 parts of a spin bath having the composition of that of Example 1. The precipitate was collected and washed with distilled water. About 18.5 parts dried product were obtained after drying.

EXAMPLES 6–14

In the following Examples 6 through 14, formaldehyde cross linked sodium lignate or sodium lignosulfonate was injected just before spinning into a stream of a viscose solution containing 8.5% cellulose, 4.85% sodium hydroxide and 2.48% sulfur. The spinning conditions were the same in all examples unless otherwise noted. The projected total denier/number of filament value was 1100/480. The viscose: cross linked polymer mixture was spun into one or the other of two spinning baths as indicated in Table II. The compositions of the spinning baths and spinning conditions were:

Bath A 8.5% $H_2SO_4$; 18.2% $Na_2SO_4$; 5% $MgSO_4$; 3% $ZnSO_4$; Temp 49°–51° C.

Bath B 5.5% $H_2SO_4$; 24% $Na_2SO_4$; 1% $ZnSO_4$; Temp. 49°–51° C.

The filaments spun into Bath B were submerged in a fresh hot water bath at 93°–95° C. after coagulation but those spun into Bath A were not.

The yarns were collected in a pot as a cake and aged 24 hours before washing and purifying by conventional procedures. The cakes were dried at 100° C. for 72 hours and allowed to cool for 4 hours before testing. The physical characteristics and elemental analysis results are recorded in Table II. The solutions at the time of spinning contain the following additive:

Example 6—Control Sample—No lignin derivative added.

Example 7—20% by weight of non-cross linked sodium lignosulfonate based on weight of cellulose in viscose solution.

Example 8—20% by weight of cross linked sodium lignosulfonate of Example 2 based on weight of cellulose in viscose solution.

Example 9—20% by weight of non-cross linked sodium lignate of Example 4 based on weight of cellulose in the viscose solution.

Example 10—40% by weight of non-cross linked sodium lignate of Example 4 based on weight of cellulose in the viscose solution.

Example 11—20% by weight of formaldehyde cross linked sodium lignate of Example 3 based on weight of cellulose in the viscose solution.

Example 12—20% by weight of formaldehyde cross linked sodium lignate of Example 3 based on weight of cellulose in the viscose solution.

Example 13—20% by weight of cyanoethylated formaldehyde cross linked sodium lignate of Example 5 based on weight of cellulose in the viscose solution.

Example 14—40% by weight of formaldehyde cross linked product of Example 3 based on the weight of cellulose in the viscose solution.

TABLE II

| Spinning | Denier | Conditioned Tenacity (GPD) | Conditioned Elongation (%) | Wet Tenacity (GPD) | Wet Elongation (%) | Yarn Microanalytical Values | | | |
|---|---|---|---|---|---|---|---|---|---|
| | | | | | | %C | %H | %S | % Na |
| Example #6* | | | | | | | | | |
| Outside of Cake | 1081 | 2.7 | 24.0 | 1.37 | 36.3 | 42.1 | 6.2 | 0.007 | 0.018 |
| Inside of Cake | 1129 | 2.64 | 28.4 | 1.32 | 37.6 | | | | |
| Example #7* | | | | | | | | | |
| Outside of Cake | 909 | 2.4 | 17.2 | 1.06 | 23.1 | | | | |
| Inside of Cake | 958 | 1.6 | 19.7 | 0.71 | 23.9 | | | | |
| Example #8* | | | | | | | | | |
| Outside of Cake | 1143 | 2.33 | 17.7 | 1.03 | 26.4*** | 42.75 | 6.08 | 0.164 | 0.24 |
| Inside of Cake | 1218 | 2.12 | 22.1 | 0.89 | 30.6 | 42.38 | 6.07 | 0.107 | 0.24 |
| Example #9* | | | | | | | | | |
| Outside of Cake | 990 | 2.31 | 17.8 | 1.47 | 29 | 43.08 | 5.99 | | |
| Inside of Cake | 1062 | 2.1 | 22.1 | 0.96 | 37 | | | | |
| Example #10* | | | | | | | | | |
| Outside of Cake | 952 | 2.01 | 14.7 | 0.93 | 23.4 | 43.06 | 5.98 | | |
| Inside of Cake | 977 | 1.68 | 17.9 | 0.68 | 21.8 | | | | |
| Example #11* | | | | | | | | | |
| Outside of Cake | 1039 | 2.24 | 18.7 | 1.07 | 31.2*** | 43.01 | 5.92 | | |
| Inside of Cake | 1112 | 2.08 | 24.9 | 1.0 | 38.6 | | | | |
| Example #12* | | | | | | | | | |
| Outside of Cake | 1040 | 2.01 | 17.9 | 0.99 | 31.1 | | | | |
| Inside of Cake | 1103 | 1.91 | 22.2 | 0.96 | 33.6 | | | | |
| Example #13* | | | | | | | | | |
| Outside of Cake | 1022 | 2.06 | 16.7 | 1.00 | 28.0 | | | | |
| Inside of Cake | 1093 | 1.97 | 21.1 | 0.93 | 29.8 | | | | |
| Example #14* | | | | | | | | | |
| Outside of Cake | 981 | 2.0 | 17.0 | 0.84 | 27.8 | 42.48 | 5.92 | | |
| Inside of Cake | 1055 | 1.87 | 22.2 | 0.79 | 33.0 | | | | |

*Spun using Bath "A"
**Spun using Bath "B"
***Secondary swelling for this sample was 72%.

It will be noted that the denier of the filament of Example 7 was much smaller than that of the control sample (Example 6) which indicates that there was virtually no retention of non-cross linked sodium lignosulfate in the fiber after coagulation. This was also true of the products of Examples 9 and 10 which contained non-cross linked sodium lignate. The deniers of these filaments were smaller than those of Examples 6, 11, 12, 13, and 14.

There was a tendency for some of the formaldehyde cross linked sodium lignosulfate and formaldehyde cross linked sodium lignate to leach from the fiber when it was treated in hot water after coagulation in spinning Bath A. For this reason, it is preferable not to pass the coagulated filament into a hot bath if the filament is spun into spinning Bath A. Loss of cross linked product is not perceptible in a hot bath following spinning Bath B.

EXAMPLE 15

An aqueous solution containing about 120 parts of distilled water and 24 parts of sodium lignate was made Nigtrogen was bubbled through the heated mixture for several hours until the evolution of ammonium and sulfur by-products had practically ceased. About 2.4 parts of paraformaldehyde were added and the mixture was refluxed for about 4 hours. Enough 21% aqueous sodium hydroxide solution was added to reduce the viscosity to a flowable solution containing the reaction product of paraformaldehyde e and sodium lignate. 144 parts of the solution were added to about 1400 parts of a spin bath having the composition of that of Example 1 and the precipitate was recovered by filtration after 30 minutes stirring. The cross linked material was washed with about 2000 parts of distilled water and was dried at a temperature of about 120° C. until the weight remained substantially constant. The solids content was about 20.1 gm. The carbon content of the product was about 67.1% and the hydrogen content was about 6.0%.

The product was insoluble in a 5% aqueous sodium hydroxide solution which is ordinarily used in making sulfur determinations. The cross linked material is, then injected into a viscose solution and spun into a conventional acid bath as in Examples 6–14 to make regenerated cellulose fibers.

EXAMPLE 16

An aqueous solution containing about 12 parts of sodium hydroxide in about 300 parts of distilled water was heated under reflux to a temperature of about 60° C. About 100 parts of sodium lignate were added in four equal portions to the solution while it was being stirred vigorously. About 2 parts of a commercially available foam preventing agent, Ocenol, were added and the mixture was filtered to remove solid particles. Nitrogen was bubbled through the heated mixture for several hours until the evolution of ammonium and sulfur by-products had practically ceased. About 105 parts of the mixture was diluted with 20 parts of distilled water. About 1.2 parts of paraaformaldehyde were added and the mixture was refluxed for about 4 hours. The reaction product of paraformaldehyde and sodium lignate was added to about 1400 parts of a spin bath having the composition of that of Example 1 and the precipitate was recovered by filtration after 30 minutes stirring. The cross linked material was washed with about 2000 parts of distilled water and was dried at a temperature of about 120° C. until the weight remained substantially constant. The solids were about 20.95 gm. This product may be injected into viscose and spun in the same manner as the previous example.

Although the invention has been described in detail for the purpose of illustration, it is to be understood that such detail is provided solely for that purpose and that variations can be made therein without departing from the spirit and scope of the invention except as it may be limited by the claim.

I claim:

1. A regenerated cellulose product containing from about 1% by weight to about 40% by weight, based on the weight of cellulose, of a sodium lignate cross linked with at least about 3.8% by weight of formaldehyde, a sodium lignosulfonate cross linked with at least about 10% by weight of formaldehyde, an aliphatic ether of the said cross linked products, or mixtures thereof which is substantially insoluble in the bath used to regenerate the cellulose from viscose wherein said sodium lignate or said sodium lignosulfonate contains not more than about 5% sulfur.

2. The product of claim 1 as a fiber.

3. The product of claim 1 containing an aliphatic ether of the formaldehyde cross linked sodium lignate or said lignosulfonate, said aliphatic ether being a reaction product of the formaldehyde cross linked sodium lignate or sodium lignosulfonate with a stochiometre amount of a compound selected from the group consisting of acrylonitrile, ethylene oxide and propylene oxide.

4. The product of claim 1, containg sodium lignate cross linked with from about 3.8% to about 10g formaldehyde.

5. The product of claim 1 containing sodium lignosulfonate cross linked with about 10 to about 20% formaldehyde.

6. The product of claim 4 containing the reaction product of cross linked sodium lignate with acrylonitrile.

* * * * *

UNITED STATES PATENT OFFICE
CERTIFICATE OF CORRECTION

Patent No. 4,215,212        Dated July 29, 1980

Inventor(s) Neal E. Franks

It is certified that error appears in the above-identified patent and that said Letters Patent are hereby corrected as shown below:

In Claim 3 at Column 10, line 5 change "stochiometre" to read --stoichiometric--.

In Claim 4 at Column 10, line 8 change "containg" to read --containing--.

In Claim 4 at Column 10, line 9 change "10g" to read --10%--.

Signed and Sealed this

Twenty-eighth Day of October 1980

[SEAL]

*Attest:*

SIDNEY A. DIAMOND

*Attesting Officer*     *Commissioner of Patents and Trademarks*